United States Patent [19]

Mais et al.

[11] Patent Number: 4,956,505

[45] Date of Patent: Sep. 11, 1990

[54] PROCESS FOR THE PREPARATION OF 4,4-DIMETHYL-1-(P-CHLOROPHENYL)-PENTAN-3-ONE

[75] Inventors: Franz-Josef Mais, Duesseldorf; Helmut Fiege; Karl-Wilhelm Henneke, both of Leverkusen, all of Fed. Rep. of Germany

[73] Assignee: Bayer Aktiengesellschaft, Leverkusen, Fed. Rep. of Germany

[21] Appl. No.: 375,761

[22] Filed: Jul. 5, 1989

[30] Foreign Application Priority Data

Jul. 20, 1988 [DE] Fed. Rep. of Germany ........ 3824518

[51] Int. Cl.$^5$ .............................................. C07C 45/62
[52] U.S. Cl. .................................... 568/316; 568/313
[58] Field of Search ...................... 568/313, 316, 318

[56] References Cited

U.S. PATENT DOCUMENTS

| | | | |
|---|---|---|---|
| 4,041,083 | 8/1977 | Gradiff et al. ...................... | 568/318 |
| 4,221,741 | 9/1980 | Gaster .................................. | 568/318 |
| 4,239,657 | 12/1980 | Nissen et al. ....................... | 568/313 |

FOREIGN PATENT DOCUMENTS

| | | | |
|---|---|---|---|
| 0038480 | 10/1981 | European Pat. Off. ............ | 568/313 |
| 0108236 | 5/1984 | European Pat. Off. ............ | 568/313 |
| 2737489 | 2/1978 | Fed. Rep. of Germany ...... | 568/313 |
| 3237478 | 4/1984 | Fed. Rep. of Germany ...... | 568/313 |
| 2253505 | 7/1976 | France ................................ | 568/313 |
| 49-43951 | 4/1974 | Japan .................................. | 568/313 |
| 761451 | 9/1980 | U.S.S.R. ............................. | 568/313 |
| 1595699 | 8/1981 | United Kingdom ................ | 568/313 |

OTHER PUBLICATIONS

Gillespie et al., Tetrahedron, vol. 31, pp. 3–8 (1975).

*Primary Examiner*—James H. Reamer
*Attorney, Agent, or Firm*—Sprung Horn Kramer & Woods

[57] ABSTRACT

4,4-Dimethyl-1-(p-chlorophenyl)pentan-3-one can be prepared by condensation of pinacolone and p-chlorobenzaldehyde in an alcohol as solvent in the presence of an inorganic base and by subsequent hydrogenation, in which the reaction mixture obtained in the condensation is hydrogenated directly without isolation of the intermediate 4,4-dimethyl-1-(p-chlorophenyl)-1-penten-3-one after the addition of a hydrogenation catalyst at elevated temperature and superatmospheric pressure to give 4,4-dimethyl-1-(p-chlorophenyl)pentan-3-one, after the hydrogenation catalyst has been separated off from the liquid hydrogenation mixture, the alcohol is largely distilled off, and the water content of the bottom product of the distillation is adjusted in such a manner that it separates into an aqueous and an organic phase, and the 4,4-dimethyl-1-(p-chlorophenyl)-pentan-3-one is recovered from the organic phase.

17 Claims, No Drawings

PROCESS FOR THE PREPARATION OF 4,4-DIMETHYL-1-(P-CHLOROPHENYL)PENTAN-3-ONE

BACKGROUND OF THE INVENTION

1. Field of the Invention

The present invention relates to a process for the preparation of 4,4-dimethyl-1-(p-chlorophenyl)pentan-3-one by condensation of pinacolone with p-chlorobenzaldehyde to give 4,4-dimethyl-1-(p-chlorophenyl)-1-penten-3-one, followed by hydrogenation of the latter. The process $ product serves as intermediate for the preparation of active compounds in plant protection and in the pharmaceutical sector (DE-OS (German Published Specification) 2,737,489, DE-OS (German Published Specification) 3,315,510, DE-OS (German Published Specification) 3,315,681).

2. Description of the Related Art

The condensation of pinacolone with substituted benzaly dehydes is known (Arch. Pharm. (Weinheim) 311 (1978), 604; Tetrahedron 31 (1975), 3); it leads to 4,4-dimethyl-1-aryl-1-penten-3-ones. In Example 1b Published Specification) 3,237,476, a procedure is described, according to which p-chlorobenzaldehyde and pinacolone are refluxed in the presence of sodium hydroxide in ethanol for 12 hours, the solvent ethanol is then evaporated, and the residue is taken up in water/methylene chloride. After acidification the pentenone is isolated from the methylene chloride phase by evaporation. The yield in that procedure is only 59% of crude product. Apart from the poor yield, the complicated aqueous work up is a disadvantage. In DE-OS (German Published Specification) 2,737,489, a procedure is described, according to which p-chlorobenzaldehyde is reacted with pinacolone in the presence of sodium hydroxide in methanol/ethanol at maximum temperatures of up to 25° C. 4,4-Dimethyl-1-(p-chlorophenyl)-1-penten-3-one is formed as a solid, has to be filtered off with suction and washed with further solvent. The required low temperature results in an inhomogeneous, partially solid reaction mixture, which can only be stirred with difficulty. Furthermore, molar amounts of sodium hydroxide have to be used. A further disadvantage is that the portions of the reaction product which remain in the mother liquor have to be isolated in an additional workup step. To hydrogenate the double bond, the pentenone is dissolved in ethyl acetate and reacted with about 26% by weight of Raney nickel and with hydrogen at atmospheric pressure and a reaction time of about 14 ½ hours. The very large amount of catalyst and the very long reaction time are the crucial disadvantages of this process. In all known procedures, the condensation product of pinacolone and p-chlorobenzaldehyde has to be isolated and purified as a solid and is only then subjected to hydrogenation in a second separate operation.

SUMMARY OF THE INVENTION

A process for the preparation of 4,4-dimethyl-1-(p-chlorophenyl)pentan-3-one by condensation of pinacolone and p-chlorobenzaldehyde in an alcohol as solvent in the presence of an inorganic base and subsequent hydrogenation has now been found, which is characterized in that (a) the reaction mixture obtained in the condensation is hydrogenated directly without isolation of the intermediate 4,4-dimethyl-1-(p-chlorophenyl)-1-penten-3-one after the addition of a hydrogenation catalyst at elevated temperature and superatmospheric pressure to give 4,4-dimethyl-1-(p-chlorophenyl)pentan-3-one, (b) after the hydrogenation catalyst is separated off from the liquid hydrogenation mixture, the alcohol is largely distilled off, and the water content of the bottom product of the distillation is adjusted in such a manner that it separates into an aqueous and an organic phase and (c) 4,4-dimethyl-1-(p-chlorophenyl)pentan-3-one is recovered from the organic phase.

DETAILED DESCRIPTION OF THE INVENTION

According to the invention, any desired ratios of pinacolone and p-chlorobenzaldehyde can be reacted. To avoid the workup of unnecessarily large excess amounts, in general 1–1.1 moles of pinacolone are used per mole of p-chlorobenzaldehyde Suitable inorganic bases are the hydroxides or carbonates of alkali metals or alkaline earth metals, for example sodium hydroxide, potassium hydroxide, magnesium hydroxide, calcium hydroxide, sodium carbonate, and potassium carbonate; preferably, sodium hydroxide or potassium hydroxide are used. Further suitable bases are the oxides of the elements mentioned which under the reaction conditions can form the hydroxides or carbonates.

The amount of the base to be added can vary within wide limits. However, it has been found that 5–30 equivalent preferably 10–15 equivalent %, of base, relative to the amount of p-chlorobenzaldehyde, are sufficient and thus help to avoid an unnecessarily high consumption of base.

The bases can be added to the reaction mixture either as such or in dissolved form. They are preferably used in dissolved form.

The alcohols used can be monohydric or polyhydric; monohydric alcohols are preferred. Alcohols which have too large an alkyl or aryl group are less favourable. Therefore $C_1$–$C_3$ alcohols, such as methanol, ethanol, propanol or isopropanol, preferably methanol, are preferably used. The amount of solvent is preferably chosen such that the reaction mixture is completely liquid during the reaction. This depends, in a manner known to one skilled in the art, also on the reaction temperature chosen. The amount of the alcoholic solvent is in general 10–80% by weight, preferably 15–60% by weight, particularly preferably 20–40% by weight, of The reaction temperature can in general be chosen within a wide range. At lower temperatures, for example down to the solidification point of the solvent, there is, however, the danger that some of the mixture crystallizes; at higher temperatures, there is the danger of byproduct formation. Therefore, the reaction is preferably carried out at 50–85° C., particularly preferably at 60–75° C.

The condensation of the pinacolone with p-chlorobenzaldehyde is, for example, carried out in such a manner that the solvent together with the desired base and one of the two reactants is initially introduced and the other reactant is metered in. Preferably, the entire amount of pinacolone is initially introduced and p-chlorobenzaldehyde is metered in. After the addition of p-chlorobenzaldehyde, preferably an additional reaction time of 1-3 hours is allowed for. The reaction mixture thus obtained from the condensation is subjected to hydrogenation in completely liquid form. If it is necessary to add more solvent for maintaining the completely liquid state, preferably the same solvent which was used in the condensation is chosen. Even after the addition of more solvents, their content in the reaction mixture should not be above 80% by weight, preferably not above 60% by weight.

The hydrogenation can be carried out in the alkaline reaction mixture or in the previously completely or partially neutralized reaction mixture. It is preferred to add such an amount of acid that 50-75% of the base present is neutralized. The acids which can be used are inorganic acids, such as hydrochloric acid, nitric acid, sulphuric acid, phosphoric acid or carbonic acid, or organic acids, such as formic acid, acetic acid, propionic acid or oxalic acid.

Suitable hydrogenation catalysts are in principle all catalysts known from the literature, as long as they do not cause side reactions. Preferably, Raney nickel is chosen, to which compounds of divalent sulphur, preferably thiodiglycol (bis(2-hydroxyethyl) sulphide) can be added to further avoid side reactions. The amount of hydrogenation catalyst chosen is in general 1-10% by weight, preferably 4-6% by weight, relative to the condensation product. About 3-20% by weight, preferably 6-10% by weight, relative to the hydrogenation catalyst, of the divalent sulphur compound is chosen.

According to the invention, the hydrogen pressure is 5-500 bar, preferably 10-400 bar, particularly preferably 100-300 bar.

The hydrogenation temperature chosen is 50-130° C., preferably 80-120° C.

After the hydrogenation, the reaction mixture is freed from the hydrogenation catalyst by customary separation methods, such as filtration, decanting or centrifugation. A hydrogenation mixture which in its entirety is in general liquid is then present. According to the invention, the alcohol is largely distilled off from this mixture. This distillation is carried out in such a manner that the bottom product of the distillation, due to its water content, separates into an aqueous and an organic phase. The water enters the reaction mixture in the form of water of reaction during the condensation, in the form of water of dilution of the base, in the form of water of dilution of the acid used for the complete or partial neutralization and also in the form of water of reaction during the neutralization. If the water content is not sufficient to allow separation into two phases, further water can additionally be added. In the case where water leaves the reaction mixture during the distillation of the alcohol, this water must also be replaced; this is in particular necessary in the case of alcohol/water azeotropes. The alcohol content in the reaction mixture after the distillation is less than 2% by weight, preferably less than 0.5% by weight, of the entire reaction mixture. The water content of the bottom product of the distillation is in particular such that all of this bottom product (organic and aqueous phase) is liquid. The water content of the reaction mixture is maintained at such a level that it is 5-30% by weight, preferably 7-15% by weight, relative to the total amount of the reaction mixture before the distillation of the alcohol.

The mixture which is present after the distillation of the alcohol and is liquid in its entirety separates into an aqueous and an organic layer. The two layers can be separated from one another by any methods customary in industry, for example by simple settling in a vessel, by using a separating flask with or without internal fittings which facilitate phase separation, or by using separators based on the principle of centrifugation.

To maintain the reaction mixture to be separated in its entirety as a liquid, the phase separation is carried out at a temperature above room temperature. A temperature above 50° C. is preferred, and particularly preferred is one above 80° C. The upper temperature limit is given by the boiling point of the aqueous phase, although it is unfavourable to carry out the separation in the proximity of this boiling point. The upper limit of the temperature is therefore at a maximum of 100° C., preferably at a maximum of 90° C.

The water-soluble components of the reaction mixture are present in the aqueous phase which has been separated off. These are the ions of the catalyst base of the condensation step which was added and of the acid which may have been added later for complete or partial neutralization. Other possible components of the aqueous phase are acidic minor components of the starting materials and also the anion of p-chlorobenzoic acid, which is formed as a byproduct. This p-chlorobenzoic acid can be isolated as a further reaction product by acidification.

After the separation procedure, the organic phase consists mainly of 4,4-dimethyl-1-(p-chlorophenyl)pentan-3-one. By simply distilling over pentanone, it is initially possible to remove all high-boiling components; this can be followed by a fractional distillation. However, it is also possible to carry out directly a fractional distillation. This fractional distillation leads to any desired degree of purity of the pentanone in a manner known to one skilled in the art.

According to the invention, 4,4-dimethyl-1-(p-chlorophenyl)pentan-3-one is obtained in 90% of the theoretical yield.

The process according to the invention can be carried out continuously, batchwise or in part continuously. The process according to the invention has a number of unexpected advantages compared with the known procedures:

1. Thus, it is very advantageous to avoid the isolation of the intermediate 4,4-dimethyl-1-(p-chlorophenyl)-1-penten-3-one, which is solid at
room temperature. This is made possible according to the invention by using the crude condensation mixture for the hydrogenation.

2. It is definitely surprising that the crude pentenone can be hydrogenated in the form mentioned without any significant side reactions.

3. A further advantage of the process according to the invention is the phase separation described into an aqueous and an organic phase. This removes the catalyst base from the condensation step in a manner which is favourable in terms of process engineering and furthermore takes almost all soluble impurities out of the organic phase.

4. It is furthermore extremely surprising that the organic phase can be distilled after the separation procedure virtually without decomposition. This could not be expected in accordance with the prior art, since a distillation of the entire mixture without separating of the aqueous phase leads to partial decomposition in the bottom product of the distillation and to a large loss in yield (see Comparative Example).

5. A significant advantage of the process according to the invention resides in the fact that at any time only liquid reaction mixtures are present, which are easy to handle in terms of process engineering.

6. 4,4-Dimethyl-1-(p-chlorophenyl)pentan-3-one is obtained in a high yield and high purity upon workup by distillation.

The examples which follow are intended to illustrate the process according to the invention, but without limiting it thereto.

EXAMPLE 1

1000 parts by weight of pinacolone, about 96% pure, were mixed with 1080 parts by weight of methanol and 100 parts by weight of an aqueous concentrated sodium hydroxide solution (about 48% strength NaOH) at room temperature, and the mixture was heated with stirring to 65–70° C. 1320 parts by weight of p-chlorobenzaldehyde were metered in as a melt over a period of 2 hours. Stirring at 65–70° C. was continued for another 2 hours, and 100 parts by weight of watermoist Raney nickel (about 50 parts by weight of dry Raney nickel) and 5 parts by weight of thiodiglycol were added, and the mixture was heated to 80° C. with the addition of hydrogen having a final pressure of 150 bar. After the absorption of hydrogen was completed after 20 minutes, the catalyst was filtered off, and the methanol was distilled off through a short column. 150 parts by weight of water, relative to the original 1000 parts by weight of pinacolone, were added to the bottom product. The mixture was transferred at 80° C. to a settling vessel and the aqueous bottom layer was separated off. The organic phase was distilled through a simple distillation apparatus.

Weight of the product: 2000 parts by weight, purity:96%;

Yield: 91% of the theoretical yield.

To increase the purity, the product can be distilled through a column.

EXAMPLE 2

The process of Example 1 was repeated with the following changes:

After the addition of Raney nickel and thiodiglycol, the hydrogenation was carried out at 10 bar instead of 150 bar of hydrogen pressure.

Duration of the absorption: 160 minutes

After the methanol distillation, 160 parts by weight of water were added, and the mixture was separated at 90° C. in a settling vessel.

Weight of the product: 1925 parts by weight, purity: 97.0%;

Yield: 88.5% of the theoretical yield

EXAMPLE 3

The process of Example 1 was repeated with the following change:

60 parts by weight of concentrated hydrochloric acid were added before the addition of the hydrogenation catalyst Raney nickel.

Weight of the product: 2015 parts by weight, purity: 96.3%;

Yield: 92% of the theoretical yield.

EXAMPLES 4–5

The process of Example 3 was repeated, except that 60 parts by weight of 50% strength aqueous sulphuric acid were added.

Yield: 89.3% of the theoretical yield.

Example 3 was again repeated, except that 35% by weight of glacial acetic acid were added.

Yield: 90.5% of the theoretical yield.

EXAMPLE 6

The process of Example 1 was repeated with the following changes:

The hydrogenation catalyst was filtered off and 200 parts by weight (relative to the original 1000 parts by weight of pinacolone) of water were added.

The solvent methanol was distilled off and the mixture was separated by centrifugation at about 65–75° C.

Weight of the product: 1970 parts by weight, purity: 97.5%;

Yield: 91% of the theoretical yield.

EXAMPLE 7 (COMPARATIVE EXAMPLE)

The process of Example 1 was repeated with the following change:

After the distillation of the solvent methanol, no water was added, and the entire mixture was distilled through a simple distillation apparatus.

Weight of the product: 1750 parts by weight, purity: 93.4%;

Yield: 77.5% of the theoretical yield.

What is claimed is:

1. In a process for the preparation of 4.4-dimethyl-1-(p-chlorophenyl)pentan-3-one by condensation of pinacolone and p-chlorobenzaldehyde in an alcohol as solvent in the presence of an inorganic base and subsequent hydrogenation the improvement comprising
   (a) hydrogenating the reaction mixture obtained in the condensation directly without isolation of the intermediate 4,4-dimethyl-1-(p-chlorophenyl)-1-pentan-3-one said hydrogenation being conducted in the presence of a Raney Nickel to which compounds of divalent sulphur are added hydrogenation catalyst at a temperature of about 50–130° C. and superatmospheric pressure to give 4,4-dimethyl-1-1-1-(p-chlorophenyl) pentan-3-one,
   (b) separating the hydrogenation catalyst off from the liquid hydrogenation mixture, largely distillijng off the alcohol, and adjusting the water content of the bottom product of the distillation in such a manner that te distillation mixture separates into an aqueous and an organic phase and
   (c) recovering 4,4-dimethyl-1-(p-chlorophenyl)pentan-3-one from the organic phase.

2. The process according to claim 1, wherein the inorganic base is an hydroxide or carbonate of alkali metals or alkaline earth metals.

3. The process according to claim 2, wherein the inorganic base is sodium hydroxide or potassium hydroxide.

4. The process according to claim 1, wherein 3–30 equivalent % of base, relative to the amount of p-chlorobenzaldehyde are used.

5. The process according to claim 4, wherein 10–15 equivalent % of base, relative to the amount of p-chlorobenzaldehyde are used.

6. The process according to claim 1, wherein the condensation of pinacolone and p-chlorobenzaldehyde is carried out at 50–85° C.

7. The process according to claim 6, wherein the condensation is carried out at 60–75° C.

8. The process according to claim 1, wherein the alcohol is a monohydric $C_1$-$C_3$-alcohol.

9. The process according to claim 8, wherein the alcohol is methanol.

10. The process according to claim 1, wherein the amount of the alcoholic solvent is 10–80% by weight of the entire reaction mixture.

11. The process according to claim 10, wherein the amount of the alcoholic solvent is 15-60% by weight of the entire reaction mixture.

12. The process according to claim 1, comprising adding after the condensation such an amount of acid that 50-75% of the entire amount of the inorganic base contained in the mixture is neutralized.

13. The process according to claim 1, wherein the hydrogenation is carried out at a hydrogen pressure of 5–500 bar.

14. The process according to claim 1, wherein before the distillation of the alcohol the hydrogenated reaction mixture contains 10–30% by weight of water, relative to the total amount of the mixture.

15. The process according to claim 1, wherein after the hydrogenation catalyst has been separated off, the phase separation is carried out at 50–100° C.

16. The process according to claim 15, wherein the phase separation is carried out by continous centrifugation in a separator.

17. The process according to claim 1, wherein 1–1.1 moles of pinacolone are used per mole of p-chlorobenzaldehyde.

* * * * *

UNITED STATES PATENT AND TRADEMARK OFFICE
CERTIFICATE OF CORRECTION

PATENT NO.   : 4,956,505

DATED        : September 11, 1990

INVENTOR(S)  : Mais et al.

It is certified that error appears in the above-identified patent and that said Letters Patent is hereby corrected as shown below:

Col. 6, line 36      Delete " pentan " and substitute -- penten --

Col. 6, lines 38-39  Delete " hydrogenation catalyst "

Col. 6, line 41      After " yl " delete " 1-1- "

Col. 6, line 43      Delete " distillijng " and substitute -- distilling --

Col. 6, line 46      Delete " te " and substitute -- the --

Col. 6, line 51      Delete " an " and substitute -- a --

Signed and Sealed this

Eleventh Day of August, 1992

Attest:

DOUGLAS B. COMER

*Attesting Officer*     *Acting Commissioner of Patents and Trademarks*